US012235004B2

(12) United States Patent
Reeves et al.

(10) Patent No.: US 12,235,004 B2
(45) Date of Patent: Feb. 25, 2025

(54) SENSOR NETWORK FOR VALIDATION OF HEALTHY BUILDINGS AND TRANSPORTATION SYSTEMS

(71) Applicant: The George Washington University, Washington, DC (US)

(72) Inventors: Mark Reeves, Arlington, VA (US); Rahul Simha, Springfield, VA (US); Chen Zeng, Washington, DC (US); Ali Eskandarian, Washington, DC (US)

(73) Assignee: The George Washington University, Washington, DC (US)

( * ) Notice: Subject to any disclaimer, the term of this patent is extended or adjusted under 35 U.S.C. 154(b) by 86 days.

(21) Appl. No.: 17/390,533

(22) Filed: Jul. 30, 2021

(65) Prior Publication Data

US 2022/0034540 A1    Feb. 3, 2022

Related U.S. Application Data

(60) Provisional application No. 63/058,835, filed on Jul. 30, 2020.

(51) Int. Cl.
*F24F 11/49* (2018.01)
*F24F 11/74* (2018.01)
(Continued)

(52) U.S. Cl.
CPC .............. *F24F 11/49* (2018.01); *F24F 11/74* (2018.01); *F24F 11/89* (2018.01); *G05B 15/02* (2013.01); *G16H 70/60* (2018.01)

(58) Field of Classification Search
CPC .. F24F 11/49; F24F 11/74; F24F 11/89; F24F 6/14; F24F 8/10; F24F 11/56; F24F 2110/64; F24F 2110/66; F24F 2110/72; F24F 2110/74; F24F 2120/10; G16H 70/60; G16H 50/50; G16H 10/40; G16H 20/13; G16H 40/20; G16H 50/80; Y02B 30/54; Y02B 30/70
See application file for complete search history.

(56) References Cited

U.S. PATENT DOCUMENTS

2012/0275952 A1* 11/2012 Lukasik .................. A61L 2/208
                                                        422/291
2016/0274025 A1*  9/2016 Skibo ...................... G06N 3/006
(Continued)

OTHER PUBLICATIONS

"Respiratory Pathogen Emission Dynamics", Coronavirus (COVID-19), Jama, Video 1 min 23 sec, available at <https://edhub.ama-assn.org/jn-learning/video-player/18357411>, Published Online, Mar. 26, 2020, 4 pages.

(Continued)

*Primary Examiner* — Tameem D Siddiquee
(74) *Attorney, Agent, or Firm* — BLANK ROME LLP

(57) ABSTRACT

Systems and methods are disclosed for air flow optimization. In certain embodiments, the technology is a system comprising sensors, injectors, actuators, and a system processor. In order to optimize the air flow, the system processor directs the injectors to expel aerosol particles into an environment, such that the aerosol particles can be measured by the one or more sensors. Flow intensity map generation is then used to map the aerosol particles and air flow is changed to optimize aerosol particle concentration using the actuators.

21 Claims, 15 Drawing Sheets

(51) Int. Cl.
*F24F 11/89* (2018.01)
*G05B 15/02* (2006.01)
*G16H 70/60* (2018.01)

(56) References Cited

U.S. PATENT DOCUMENTS

2018/0363023 A1* 12/2018 Kingsley ................. C12N 15/02
2019/0331701 A1* 10/2019 Polley ................. G01N 35/0099
2021/0011443 A1* 1/2021 Mcnamara ........... F24F 11/0001

OTHER PUBLICATIONS

Bourouiba, Lydia, "Turbulent Gas Clouds and Respiratory Pathogen Emissions Potential Implications for Reducing Transmission of COVID-19", Clinical Review & Education, JAMA, vol. 323, No. 18, May 12, 2020, pp. 1837-1838.

Culver, Jordan, "2 Meters Enough for Social Distancing? Mit Researcher Says Droplets Carrying Coronavirus Can Travel Up to 8 Meters", Medical Xpress, News, available at <https://medicalxpress.com/news/2020-04-meters-social-distancing-mit-droplets.html>, Apr. 1, 2020, 5 pages.

Farhan, et al., "A Concise Review on Internet of Things (IOT) - Problems, Challenges and Opportunities", 11th International Symposium on Communication Systems, Networks & Digital Signal Processing (CSNDSP), 2018, 6 pages.

Kalliomaki, et al., "Airflow Patterns Through Single Hinged and Sliding Doors in Hospital Isolation Rooms - Effect of Ventilation, Flow Differential and Passage", Building and Environment, vol. 107, 2016, pp. 154-168.

Ong, et al., "Air, Surface Environmental, and Personal Protective Equipment Contamination by Severe Acute Respiratory Syndrome Coronavirus 2 (SARS-COV-2) From a Symptomatic Patient", JAMA, vol. 323, No. 16, 2020, pp. 1610-1612,.

Petrov, Dmitry, "Photopolarimetrical Properties of Coronavirus Model Particles: Spike Proteins No. Influence", Journal of Quantitative Spectroscopy & Radiative Transfer, vol. 248, 2020, 9 pages.

Patrick et al., How to Transform Your Learning Environments for COVID-19, Sasaki Associates, Inc., May 19, 2020, 15 pages.

* cited by examiner

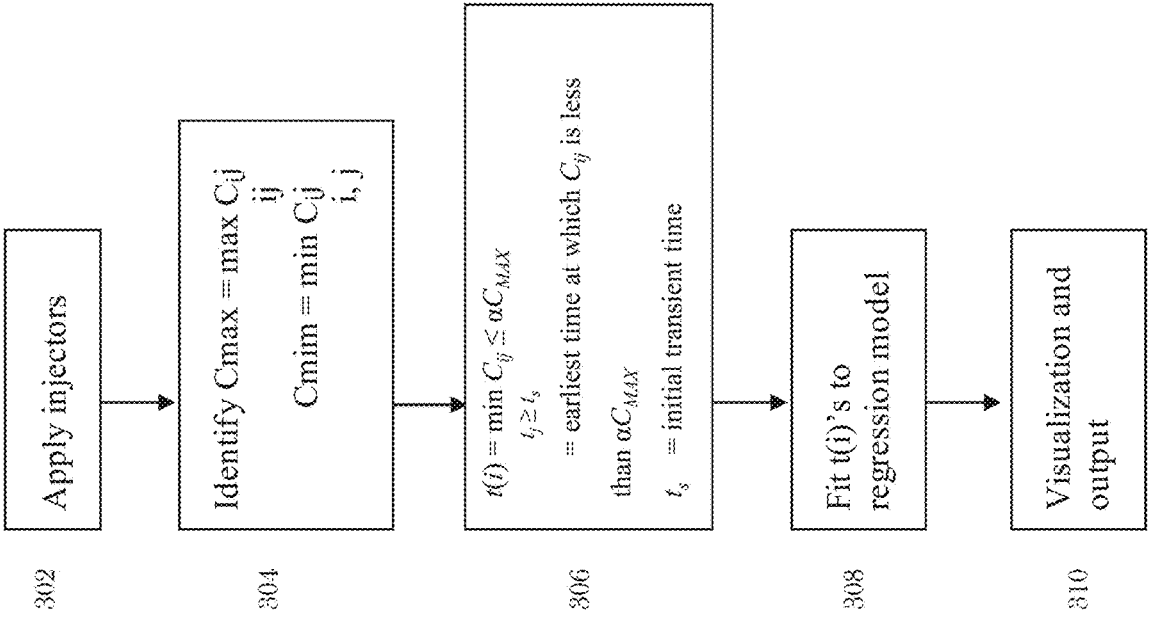

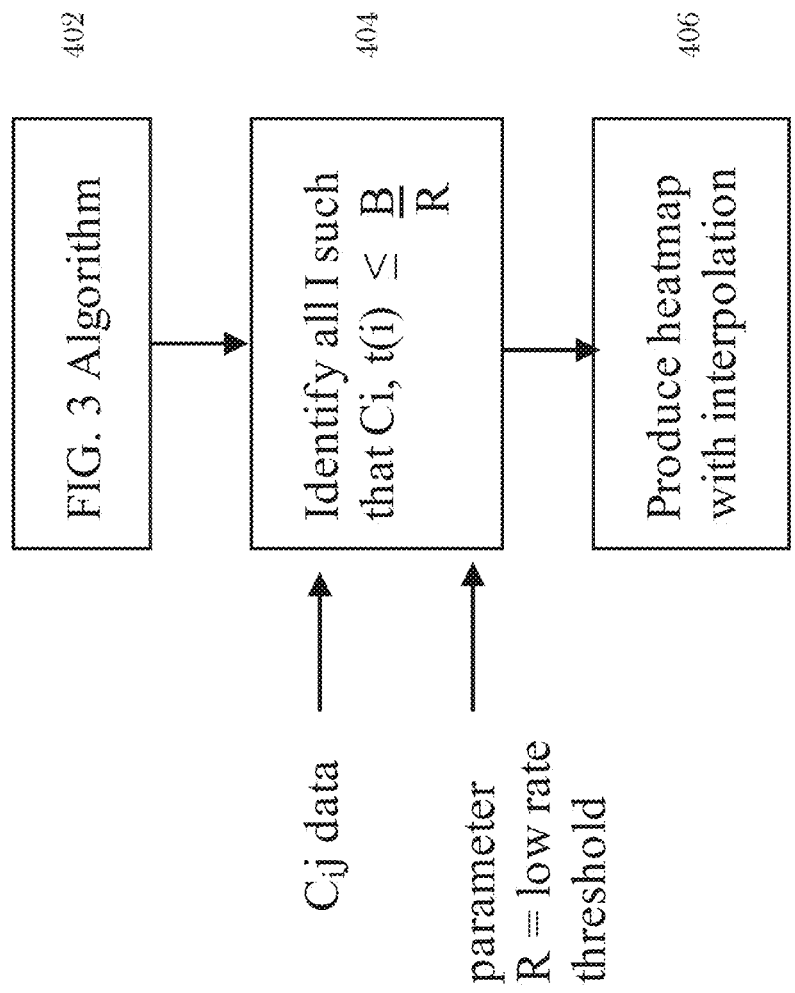

SENSOR NETWORK FOR VALIDATION OF HEALTHY BUILDINGS AND TRANSPORTATION SYSTEMS

CROSS-REFERENCE TO RELATED APPLICATIONS

This application claims the benefit of priority of U.S. Application Ser. No. 63/058,835 filed Jul. 30, 2020, the content of which is relied upon and incorporated herein by reference in its entirety.

FIELD OF THE DISCLOSURE

The field of the disclosure relates to monitoring and optimizing air flow in a closed environment. More specifically, the technology relates to monitoring aerosol particles in a closed environment and altering air flow to optimize their concentration.

BACKGROUND OF THE DISCLOSURE

The average American spends 90% of their time indoors, breathing air that is conditioned in ways that often do not consider health. In the mid 1970's, air-exchange standards were cut in half to save energy, as a result, respiratory disease incidence rose. COVID-19 reminds us once more that building hygiene is essential for human health. Current safety standards for new buildings mandate 3 air exchanges per hour, increased to 6-9 air exchanges per hour during the COVID-19 pandemic. Empirical observations of injected fog by stop action photography have traditionally provided evidence for clearance capabilities of air exchange, as shown in the work of Kalliomäki and others (Petri Kalliomäki1, Pekka Saarinen1, Julian W Tang and Hannu Koskela, Airflow Patterns through Single Hinged and Sliding Doors in Hospital Isolation Rooms, International Journal of Ventilation ISSN 1473-3315 Volume 14 No 2 Sep. 2015. However, the question is: what is the quantitative evidence of the effectiveness for these mitigation efforts?

Officials in charge of rearranging and maintaining clean workspaces to comply with CDC guidelines do not have concrete data highlighting how the changes made in their workspaces have hindered or inadvertently accelerated aerosol particle perfusion. The present disclosure provides quantitative data about the effectiveness of various mitigation strategies for preventing the spread of aerosol particles in the wake of COVID-19.

Based on customer segmentation interviews, it has been shown that corporate workspace managers are most pressed to tailor their workspaces to safely reopen and require conclusive data to verify the effectiveness of their mitigation efforts before progressing further. As such, these managers are our primary focus and our initial customer segment.

The present disclosure presents a solution to such deficiencies in the art by more efficiently mapping and analyzing airflow patterns to determine mitigation measures for particulate matter in the air.

SUMMARY OF THE DISCLOSURE

The present technology maps the airflow patterns in spaces where end users and dependents constantly interact. The present disclosure includes software that handles the measurement and storage of sensor data, which is analyzed to determine how factors such as layout and HVAC configurations affect local particle concentrations. The system and method of the present disclosure ultimately informs which types of mitigation measures, such as boosting HVAC air-exchanges and filtration, partitions, external vents, and scheduling, produce desirable airflow patterns in our customer's workspaces. The adaptability of the concept allows for individual customers to maximize savings on HVAC energy costs, which coupled with airflow pattern analysis assists in development of healthy workspaces. After the desired environmental workspace conditions are determined, the sensor network is removed from the customer premises.

In certain embodiments, the technology is a system comprising sensors, injectors, actuators, and a system processor. In order to optimize the air flow, the system processor directs the injectors to expel aerosol particles into an environment, such that the aerosol particles can be measured by the one or more sensors. Flow intensity map generation is then used to map the aerosol particles and air flow is changed to optimize aerosol particle concentration using the actuators.

In other embodiments, the one or more sensors are PM2.5 sensors.

In yet other embodiments, one or more auxiliary sensors are used to detect volatile organic compounds, ozone, and $CO_2$.

In other embodiments, the system further identifies regions of low air exchange by determining geographical locations for the one or more sensors and interpolating a heatmap visualization of the low air exchange regions.

In still other embodiments, the system further comprises one or more filters, and the system processor activates the one or more filters in a manner that maintains the aerosol particle concentration within a predetermined range.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 3 is a flow diagram illustrating how the present technology performs air change per hour (ACH) estimation;

FIG. 4 is a flow diagram illustrating how the present technology performs low-exchange troublespot identification;

DETAILED DESCRIPTION OF THE PREFERRED EMBODIMENTS

Figure 1:
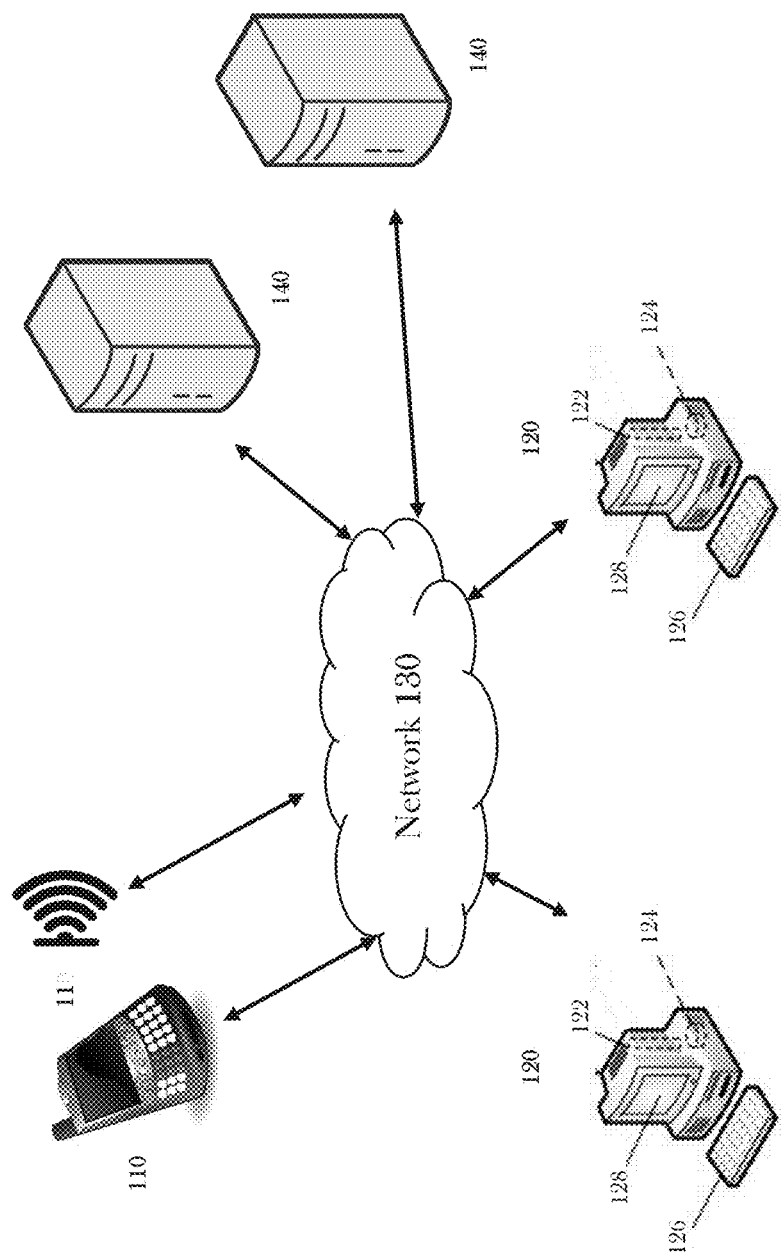
FIG. 1 is an exemplary embodiment of the hardware of the air quality validation system.

In describing a preferred embodiment of the disclosure illustrated in the drawings, specific terminology will be resorted to for the sake of clarity. However, the disclosure is not intended to be limited to the specific terms so selected, and it is to be understood that each specific term includes all technical equivalents that operate in a similar manner to accomplish a similar purpose. Several preferred embodiments of the disclosure are described for illustrative purposes, it being understood that the disclosure may be embodied in other forms not specifically shown in the drawings.

Covid-19 has made acutely clear that building hygiene, vis-a-vis the reduction of aerosol particles in indoor air is essential for human health. Current standards for new buildings mandate three air exchanges per hour, and six to nine for safety during the COVID-19 pandemic. The average American spends 90% of their time indoors, breathing air that, if improved, could yield an 8% improvement in productivity, an average of $6,500 per person. Even, looking well past the pandemic, the need will remain to maintain high-quality it is increasingly clear that indoor air.

Disclosed herein is an internet-of-things technology concept that will offer sensing technology to audit air quality, followed by mitigation consulting. It will offer three stages of technological innovation to its customers. The first is accurate distributed sensing through inexpensive wireless particle sensors installed in the customer's premises. The second will rely on in-house knowledge accumulated through laboratory experimentation to design mitigations specific to the geometry and architecture of customer buildings. The third is an analysis and recommendation tool for people movement within a building, to minimize congestion and potential infection risk (even from mild afflictions like coughs and colds that reduce productivity).

In a typical customer transaction, removable sensor assemblies are placed throughout rooms in the customer's premises to make sensing measurements The software combined with sensor feedback converts measurements into model airflows and recommend a variety of mitigation measures such as boosting HVAC air-exchanges, partitions, external vents, and scheduling. Finally, the sensor assemblies will also collect people-movement data and identify periods of congestion, offering multiple options for people movement to optimize quality airflow. After remediation, the sensors will be removed (unless the customer, such as a clinic, desires continual sensing).

Taken together, the system combines intelligent sensing and filter-activation over an entire indoor environment. Current state of the art for predicting and visualizing airflow in spaces is to use computational fluid dynamics (CFD). CFD works for fairly simple spaces but becomes costly, time consuming, and inaccurate when introducing small complications, like having people moving in the space. Our measurement system is simple, direct, and flexibly gives the right answer by design. It is an improvement over the state-of-the-art because it enables simultaneous real-time measurement in three different aspects:

Temporal. Because the injectors can be carefully timed to release aerosols at various concentrations and at various times, it is possible to build a temporally fine-grained airflow map whether in a single room or larger space.

Spatial: 3D and across the entire building. The distribution of multitudes of sensor assemblies and injectors across a whole building enables accurate reconstruction of airflows between different areas of a building and how they change over time.

Fine-grained air-clearance times. The system enables a deep quantitative understanding of how often air-exchanges are manifested in different parts of rooms and in different parts of the building.

Actuation-enabled. Finally, the system of controllable filters enables real-time response and adjustment across the whole environment. This is particularly important because people move about and affect the minute-by-minute airflows.

Portability. The entire system is designed to be packaged in boxes, with units that are portable and easily attached to ceilings and walls. Thus, unlike fixed-infrastructure solutions that only perform coarse-grained monitoring, this system may be applied for a while and easily dismantled.

The system and method of the present disclosure has a variety of applications, including, but not limited to:

High-quality, real-time monitoring and mitigation. The system can be applied in a variety of settings (schools, hospitals, office-buildings, factories, transportation systems) and specialized to the types of particles expected in those settings.

Hot-spot detection. The high spatial resolution enables narrowing down the search for hotspots inside rooms, especially high-traffic areas in hospitals and factories. Hotspots are then mitigated with the controllable filters and the mitigation efficiency monitored in real-time.

Event-triggering for evacuation. The system is also designed to identify optimal evacuation routes because the real-time monitoring enables crafting efficient and safe exit routes.

Architectural design. One of the most interesting uses is in the design of future buildings. Architectural firms can create table-top models of their buildings and apply our system to systematically study interior designs for their effectiveness in providing healthy air indoors.

Recommendation engine. Human operators carrying sensor assemblies can move around to try multiple configurations for seating. The system can be used to recommend effective patterns of seating combined with optimal placement of filters.

Transportation ventilation design/redesign. Transportation systems: busses, trains, and subway cars have ventilation systems designed for passenger comfort, not necessarily for mitigating aerosol spread throughout the passenger space. Closely placed sensors, networked together can provide real-time mapping for the spread of viral particles in densely-packed passenger compartments.

FIG. 1 is an exemplary embodiment of the hardware of the air quality validation system. In the exemplary system 100, one or more peripheral devices 110 are connected to one or more processing devices such as computers 120 through a network 130. Examples of peripheral devices 110 include sensors, injectors, filters, actuators, and any other devices that collect data that are known in the art. The network 130 may be a wide-area network, like the Internet, or a local area network, like an intranet. Because of the network 130, the physical location of the peripheral devices 110 and the computers 120 has no effect on the functionality of the hardware and software of the present disclosure. Both implementations are described herein, and unless specified, it is contemplated that the peripheral devices 110 and the computers 120 may be in the same or in different physical locations. Communication between the hardware of the system may be accomplished in numerous known ways, for example using network connectivity components such as a modem or Ethernet adapter. The peripheral devices 110 and the computers 120 will both include or be attached to communication equipment. Communications are contemplated as occurring through industry-standard protocols such as HTTP.

Each processing device or computer 120 is comprised of a system processor 122, a storage medium 124, a user-input device 126, and a display 128. Examples of computers that may be used include commercially available personal computers, open source computing devices (e.g. Raspberry Pi), commercially available servers, and commercially available portable device (e.g. smartphones, smartwatches, tablets). In one embodiment, each of the peripheral devices 110 and each of the computers 120 of the system may have the air quality validation software related to the system installed on it. In such an embodiment, data may be stored locally on the networked computers 120 or alternately, on one or more remote servers 140 that are accessible to any of the networked computers 120 through a network 130. In alternate embodiments, the air quality validation software runs as an application on the peripheral devices 110.

Figure 2A:
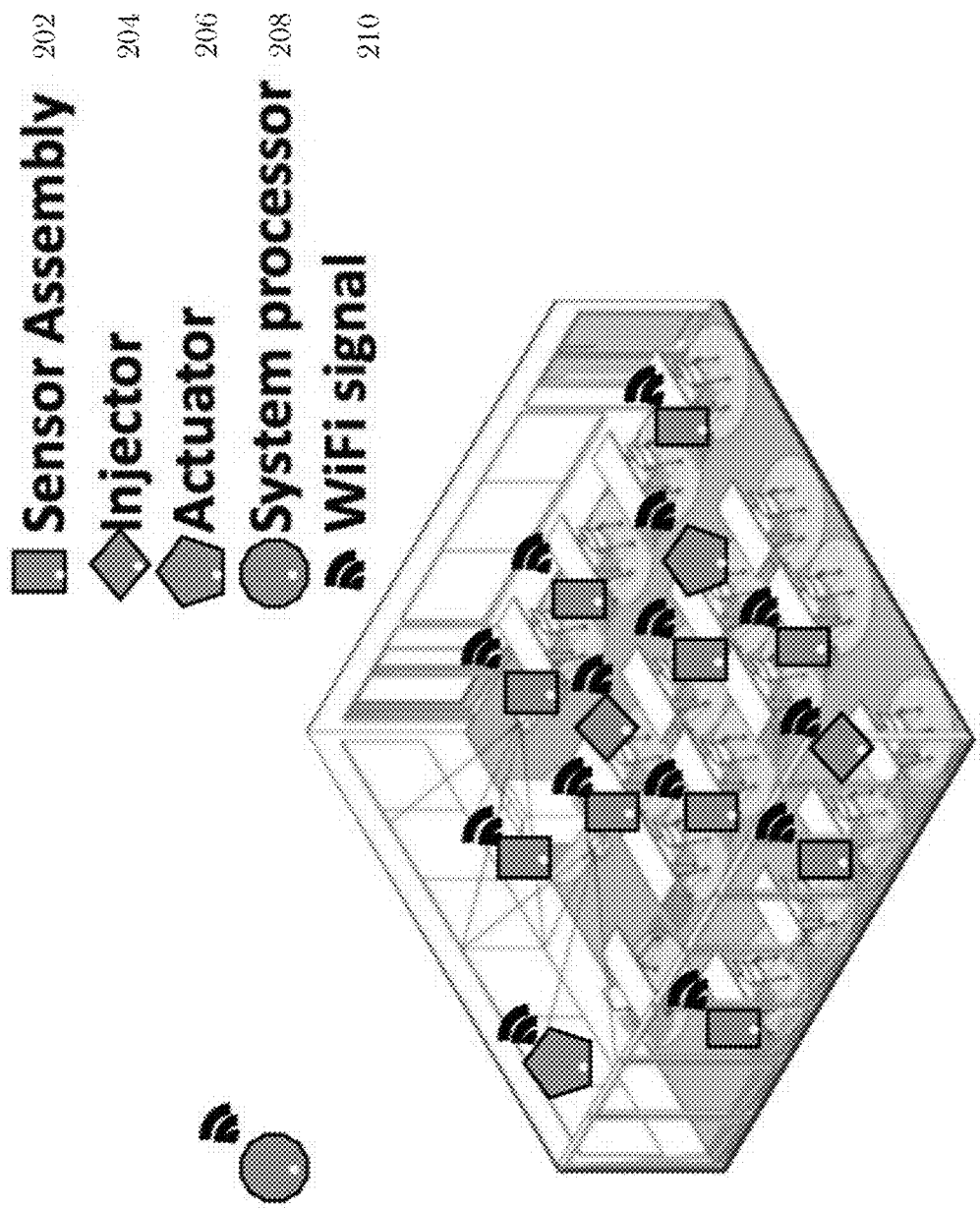
FIG. 2A is a hardware implementation of the technology in a classroom configuration.

FIG. 2A is a hardware implementation of the technology in a space, shown in the present example as a classroom configuration. In different locations in the room is a sensor assembly 202. The sensor assembly 202 is hardware of the present disclosure that includes a processor, one or more sensors, primarily PM2.5 sensors, memory to store data when off-line, and auxiliary sensors such as to detect VOCs (volatile organic compounds), ozone, or $CO_2$. In certain embodiments, the sensor may itself be comprised of an assembly a processor and a memory, thereby functioning as a sensor assembly. In certain embodiments, the sensors convert sensed electronic data into concentration data using firmware built into purchased, factory-calibrated PM2.5 sensors. The protocols require checking the calibration and adjusting the fitting polynomials, as needed for accurate measurements. The sensor assembly includes a housing that houses the processor and memory and allows for air flow to reach the sensor. The system processor 208 controls the system, and from it, commands are issued (via WiFi) 210 to turn the aerosol source(s) off and on, and to initiate synchronized measurements of aerosol particles. The system processor 208 also issues commands to control actuators 206, which change the airflow in the room. Actuators, as used herein, may refer to fans, dampers, relocatable air filters, or any other device known in the art that is able to change airflow. The system processor 208 also collects feedback from the actuators 206 related to airflow and changes to it. The feedback from the actuators 206 may be used by the system processor 208 to modulate a quantity of the aerosol particles expelled by the injectors 204, which are explained in greater detail below.

The sensor assembly 202 is one system processor hardware element. It includes one or more relatively inexpensive particle sensors, a source of aerosol particles, a microcontroller with on-board memory (e.g. Raspberry Pi or equivalent) for local control, capability to add other relevant sensors such as VOC or $CO_2$, and WiFi receiving/transmitting capability to communicate with the system processor. Sensor assemblies 202 can be battery operated, can autonomously store data for later downloading, and can operate synchronously with one or more other sensor assemblies under control of the system processor. Based on the software configuration, a sensor assembly 202 can be permanently placed to locally monitor aerosol generation, clearance, and movement. It can also be set up in a temporary configuration to map the aerosol flows in a space as conditions in the space are modified.

It is important that the system know the location of the sensors, sensor assemblies, injectors, actuators, and fixed building features (such as walls, furniture, partitions, and the location and position of vents), to report back with the concentration data. This can be done manually, as in FIGS. 12-14, by the operator recording of the sensor placement and location within the room (e.g., a horizontal position, vertical position, and height). For example, that a first sensor is positioned a first distance from a side wall, a second distance from a front wall, and a first height; and a second sensor is positioned at a third distance from the side wall, a fourth distance from the front wall, and a second height (the same or different than the first height). In other embodiments the WiFi capability of the sensor processor can triangulate (using commercially available systems) on the building's WiFi signals to accurately locate the sensors. This approach allows the sensors to be mobile.

The injector 204 is a device to put aerosol particles into the room. This can be a heated or ultrasonically driven source of water-based particles with a low percentages amount of water-soluble small molecules (like glycerin or salt) added. These devices mimic a person in the room emitting exhaled aerosol particles, in so far as they have the same physical/aerosol properties. The injector 204 is controlled by the system processor 208 directly or indirectly through code uploaded to the sensor assembly 202. It can also be manually operated and be as simple as a spray can of artificial fog.

The actuator 206 is a temporarily placed device or a permanently installed one that changes the flow of aerosol particles in the room. This device can be controlled by the system processor 208 and can be, for example, a damper, a fan, the on/off control of the HVAC system, a portable filtration unit, or a static or moveable barrier. The aerosol particle levels in the room are measured by the sensor assemblies 202 before and after actuation of the device 206, and this information is used to test the efficacy of actuation, and also to provide feedback on control of air quality response to changes in external or internal environment, examples would be change in season, changes in building occupancy, or renovations.

The system processor 208 is a desktop or laptop computer, with any of the three major operating systems (Linux, windows, or OS X). It sends via WiFi 210 commands to and receives data from the sensor assemblies, the actuators, and the injectors. The purpose and architecture of these subsystems has already been described, and the system processor is fairly simple. It communicates with the actuators and injectors in real time via a master controlling program. It communicates with the sensor assemblies either synchronously or asynchronously (depending upon the application). In the latter mode, it downloads data stored on a device like an SD card integrated into the sensor assembly 202.

Figure 2B:
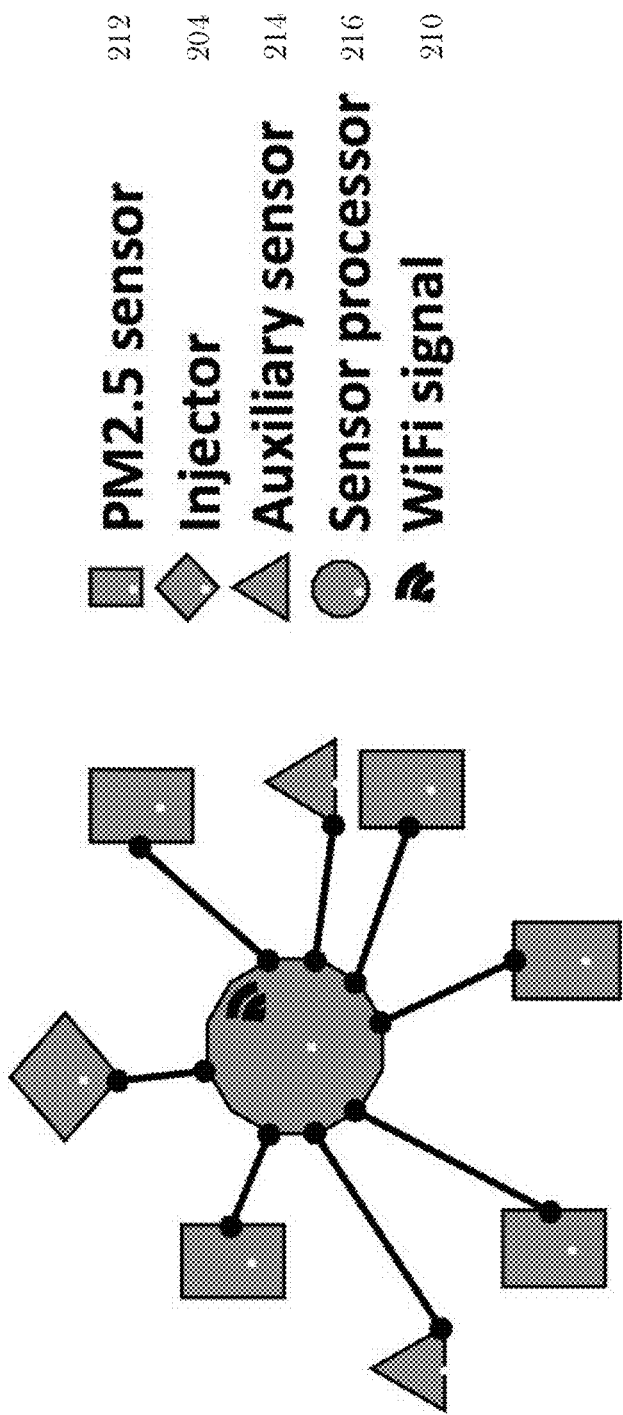
FIG. 2B is the hardware implementation of the sensor assembly in accordance with an exemplary embodiment of the technology.

FIG. 2B is one embodiment of a hardware implementation of sensor assembly. As shown, the sensor assembly includes one or more particle sensors 212 and a sensor processor 216. The assembly can further optionally include one or more injectors 204 and one or more auxiliary sensors. The particle sensors 212 detect/measure particle counts in the vicinity and downstream from the injector 204, both of which are controlled by algorithms stored in the sensor processor 216. The sensor processor 216 pre-processes the raw data detected by the sensor. Auxiliary sensors 214 allow for the measurement of important interesting quantities, not in aerosol form, like $CO_2$ or volatile organic compounds. Finally, the assembly can, in the most common configuration, communicate bidirectionally with the system processor, for example, using a WiFi signal 210. The sensor processor is in communication (wired or wirelessly) with the sensor(s) 212, injector(s) 204, and auxiliary sensor(s) 214 to receive data and to transmit command signals.

For example, the sensor 212 detects raw data, such as the particle count, and transmits the particle count to the sensor processor 216. The sensor processor 216, in turn, can perform pre-processing of that raw data and data conditioning. The sensor processor 216 can further store the pre-processed data and transmit data to the system processor 208. The system processor 208 receives data from all of the sensor processors, and performs calculations and generates outputs and reports based on the received data. The sensor processor and/or the system processor can generate command signals that are transmitted to the injector(s) and sensor(s) based on the calculations and other output. The overall system operation is performed in real-time without manual interaction, to provide a dynamic system that continually evaluates sensed data based on feedback, e.g., the injector output and actuator settings, and dynamically adjusts the injector based on that feedback. Commands that are generated by the system processor 208 can be transmitted to the sensor processor, which then controls the injector(s) and/or sensor(s) 212, 214. It is further noted that the sensor assembly can be enclosed in a common housing, or can be in separate housings. The sensor processor 216 can be separate and remotely located from the system processor 208, or can be implemented by a single processing device.

It is further noted that the system processor (and/or sensor processor) operates the injectors to perform certain operations, including for example to turn ON, turn OFF, adjust concentration, and/or adjust velocity. This allows the injector(s) to simulate events inside the room, and the system processor can then dynamically determine an impact of those events on air flow. For example, the injectors can be controlled to emit a burst (high concentration and high velocity for a limited period off time) to simulate the event of a person sneezing inside the room. The system processor can then gather information from the various sensors to determine an impact of that event, for instance how far and where the sneeze travels inside the room. Turning ON the injector allows the system processor to determine the baseline concentration and flow parameters inside the room. Turning OFF the injectors enable the system processor to determine how quickly a room is cleared once people leave the room.

Likewise, the system processor (and/or sensor processor) can operate the sensors to perform certain operations, including for example, to turn ON, turn OFF. The system processor (and/or sensor processor) can operate the actuators to perform certain operations, for example, to turn a filter fan ON, turn a filter fan OFF, adjust the fan speed. Those operations enable the system processor to determine various conditions, such as environmental impact (e.g., to maximize HVAC efficiency), background noise level, and to reduce the risk of infection.

It is further noted that the sensor assembly can operate synchronously, wherein the sensor processor is in communication with the system processor, which are in continuous communication with one another to operate in real time and dynamically. In addition, the sensor assembly can operate asynchronously, wherein the sensor processor is not in communication with the system processor. For example, communication can be broken intentionally or unintentionally (e.g., if the walls or distance between them do not permit wireless communication. In asynchronous operating mode, the sensor processor can store data and communicate that data to the system processor at a later time (not in real time), once communication is reestablished. The sensor processor can control operation of the injectors, sensors and actuators while not under control of the system processor.

FIG. 3 is a flow diagram illustrating how the present technology performs the air change per hour (ACH) estimation. One purpose of this software method is to provide the operator with a convenient high-resolution visualization of the air exchange rates in the indoor space in which the system is installed. The algorithm can also be used to automatically feed into the HVAC controls if desired. The software commences at step 302, where the system processor 208 uses the wireless network to send a message to each injector 204 to begin injection at a scheduled time (with enough time so that all injectors begin simultaneously), and a message to each sensor assembly 202 to reset and prepare to measure at the designated time. We use the term Cij to represent the measured concentration at sensor assembly i at time tj. Here, time is divided into small intervals t1, t2, t3 . . . etc. at the discretion of the installation.

At step 304, when the last measurement period completes, which is itself after the last moment of aerosol injection, each sensor applies smoothing and interpolation to condition the raw data. The sensor assembly contains a micro-CPU (e.g. Raspberry Pi) or other processing device. This process depends on the particulars of the sensor manufacturer. For example, a particular PM2.5 manufacturer may evince higher error rates and variability than others. This is one of the advantages of using intelligent sensor assemblies: each can be independently configured long after the installation and can be updated at any time. The error-corrected Cij measurements are then wirelessly transmitted to the sensor assembly to the system processor 208. At the server, the Cij data are processed to identify Cmax and Cmin as shown. Cmin is used to identify potential malfunctioning sensors and Cmax is used in the next step 306.

At step 306, an input parameter α is obtained from the user interface of the system processor at the time of installation and can be modified at any time. This parameter (input or stored) is used to compute the t(i) value for each sensor i. Note: a sensor assembly can contain multiple sensors. Informally, the t(i) value is the earliest time at which sensor i detects that the air is reasonably clear (as specified by the parameter α). Here, ts is an initial transient time which allows all devices to settle into a stable measurement, typical of most measuring devices.

At step 308, the system processor then applies a pre-stored regression model to the t(i) values to correct for errors and smooth out the estimates. The particular regression model used is selected in the server interface at install time and can be reconfigured at will. Examples of regression include time-series autoregression.

Figure 12:
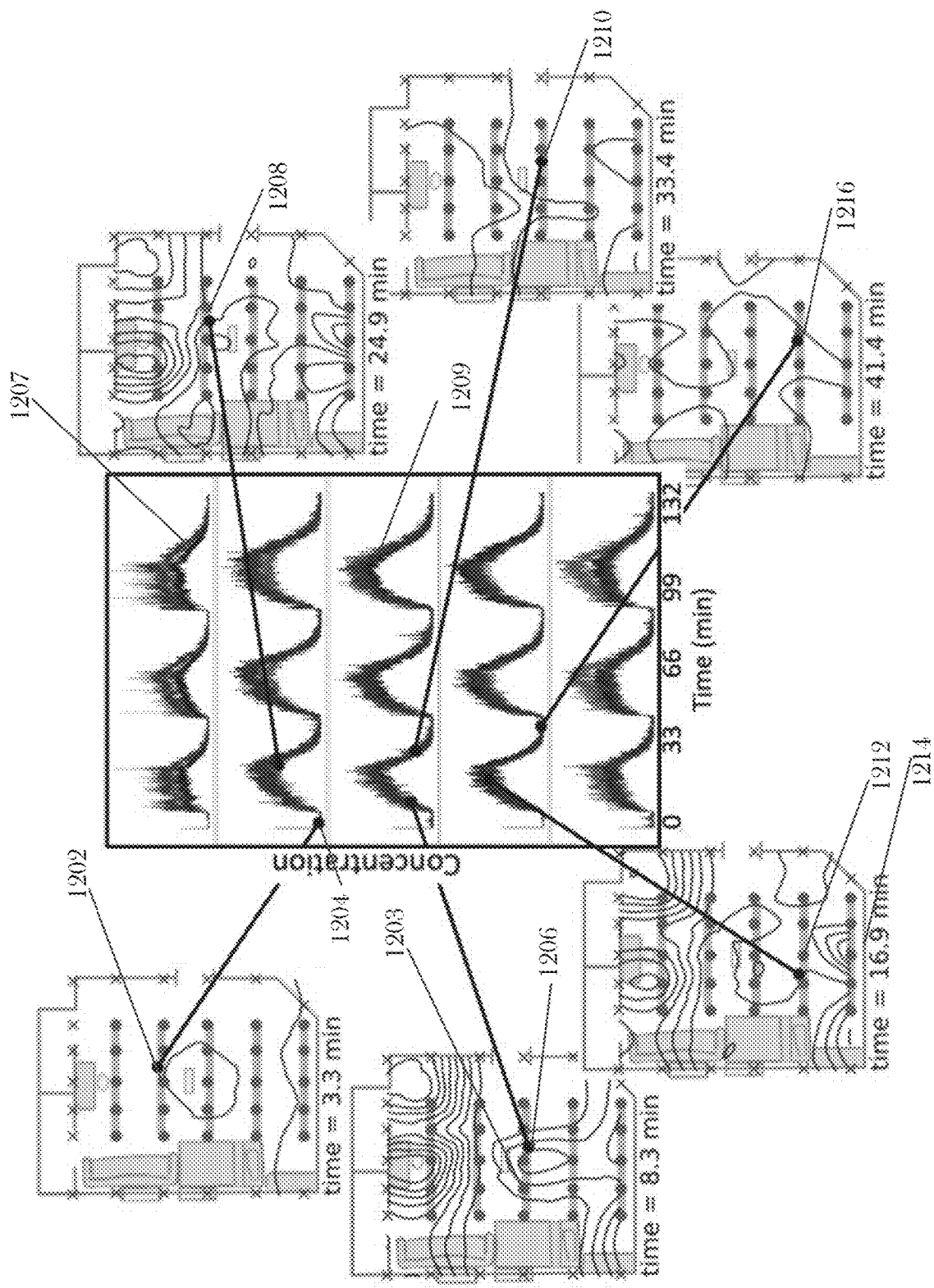
FIG. 12 is a diagram illustrating an application of the present technology to a space with low built-in airflow with a supplemental portable filter.
Figure 13:
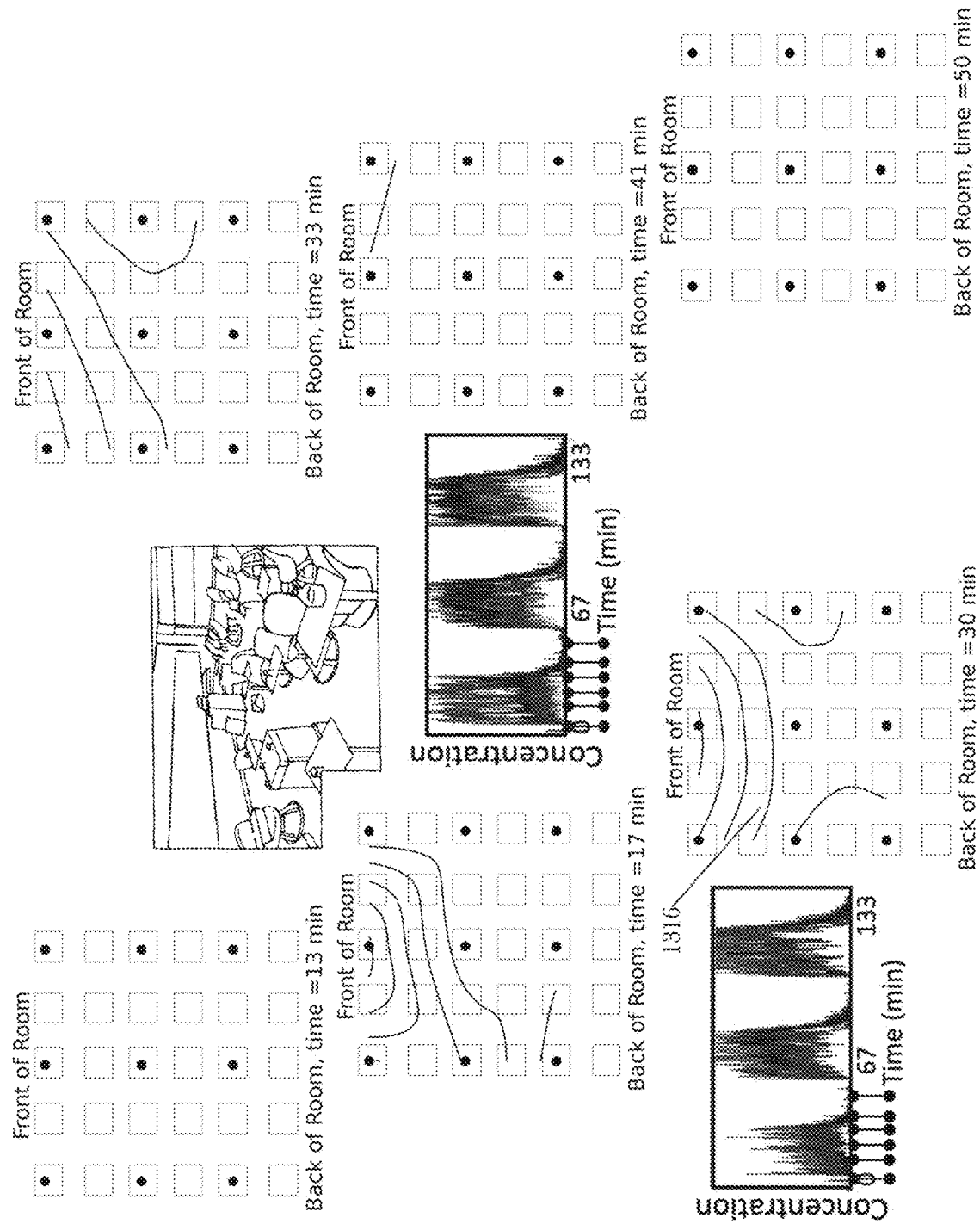
FIG. 13 is a diagram illustrating an application of the present technology to a classroom showing aerosol measurements.
Figure 14:
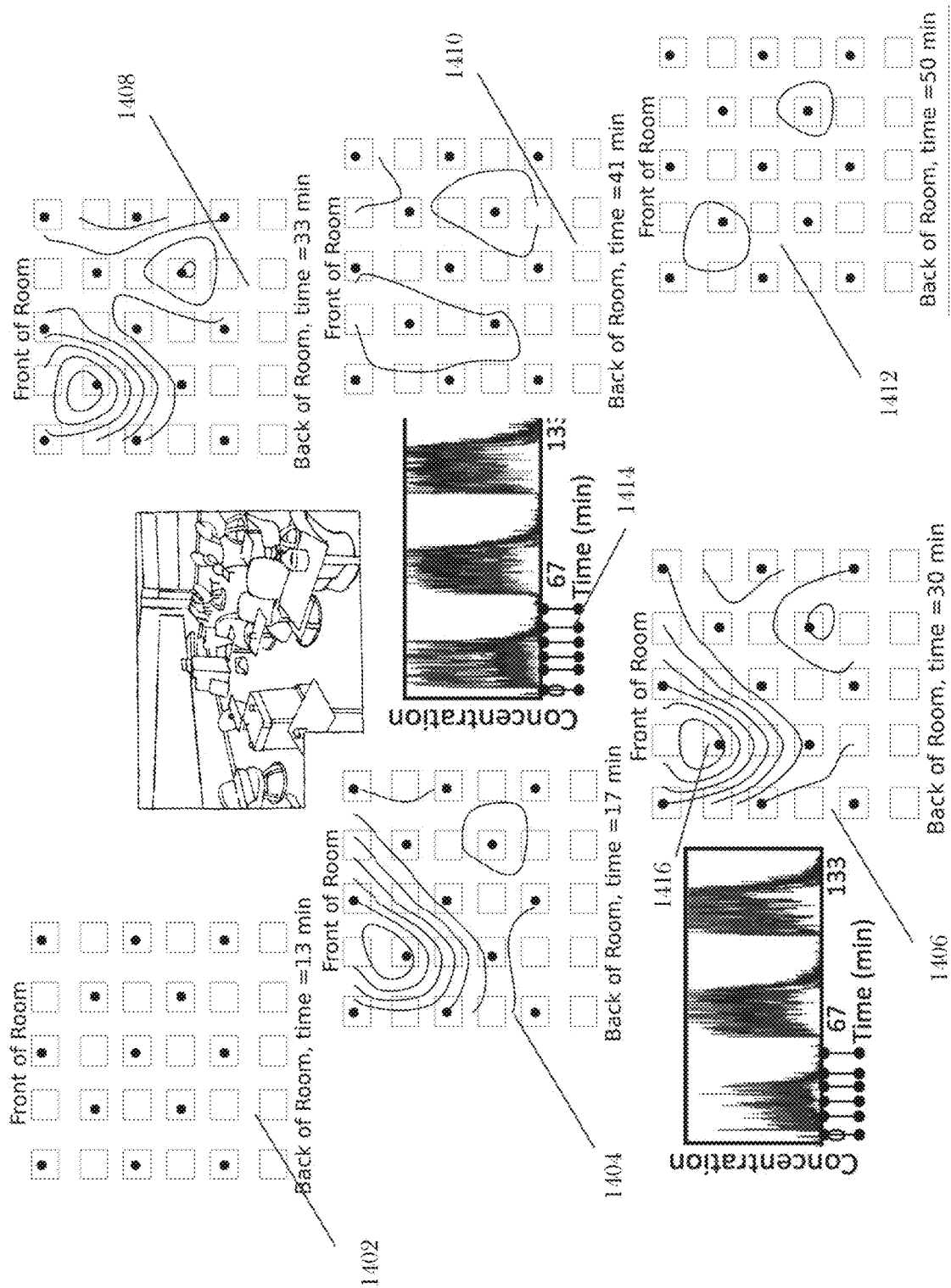
FIG. 14 is a diagram illustrating an application of the present technology to a classroom showing aerosol measurements.

At step 310, once the t(i) values are computed, the system processor 208 then uses these values to generate an electronic and/or printed report, including to interpolate colors in a heatmap. The report may also be a visualization that takes the form of a table, a graph, a video, or a chart. The heatmap overlaid on a floor plan is then depicted using graphing software, and the output stored to disk. Next, the t(i) values are compared against desired targets and past history to algorithmically issue recommendations. Such recommendations include: application of filters, adding additional sensors, and signals to the HVAC system to activate additional airflow. Finally, the estimated air-exchange rate is included in the report based on the above analysis. FIGS. 12-14, described below, are examples of graphical output reporting analyzed data. The rate at which the intensity drops with time, for example from point 1212 to point 1214 on the central graph, can be used to compute the air change per hour (ACH), a common quantity used to parameterize the entirety of how quickly particles are cleared from a room. The ACH can be observed to vary from one place in the room to another, depending upon the local air flow.

FIG. 4 is a flow diagram illustrating how the present technology performs low-exchange troublespot identification. One purpose of the method described in FIG. 4 is to provide the operator with a map of trouble spots where the air-exchange rate is consistently low over time. Because this is being done simultaneously over the full set of sensors, this process, through spatial and floor-plan interpolation can help identify particular areas for mitigation. For example, it can detect an opportunity to fix a vent or insert a new vent (intake or exhaust), or install a filter in a particular room or passageway.

At step 402, the method described in FIG. 3 is applied. At step 404, the parameter R (low rate threshold) is input from the server's user interface at install time and can be adjusted by the operator at any time. The system processor 208 already has the Cij values and t(i) values after the execution of step 402. The equation in step 404 is appended to identify all the low air-exchange trouble spots based on the suggested formula. Here, β is a parameter that controls the sensitivity with respect to the given threshold. The resulting output is generated for multiple values of β. Then, at step 406, the geographical locations of the low rate sensors are used to interpolate a heatmap visualization that is then overlaid on the floor plan. There are three types kinds of trouble spots depending upon the relationship between the source (infectious patient) and the receiver (healthy patient). The first type has extremely low air flow. Here, unhealthy concentrations can accumulate to dangerous levels and is referred to as a still spot or dead spot. The second is a high flow rate region that draws air from all parts of the room. This is referred to as a bottleneck and will be hazardous to a healthy person place there, downwind from an infected one. The third type is a related bottleneck and results from an infectious person placed there, upwind from healthy people. More details are given in the descriptions of FIGS. 12-14.

Figure 5:
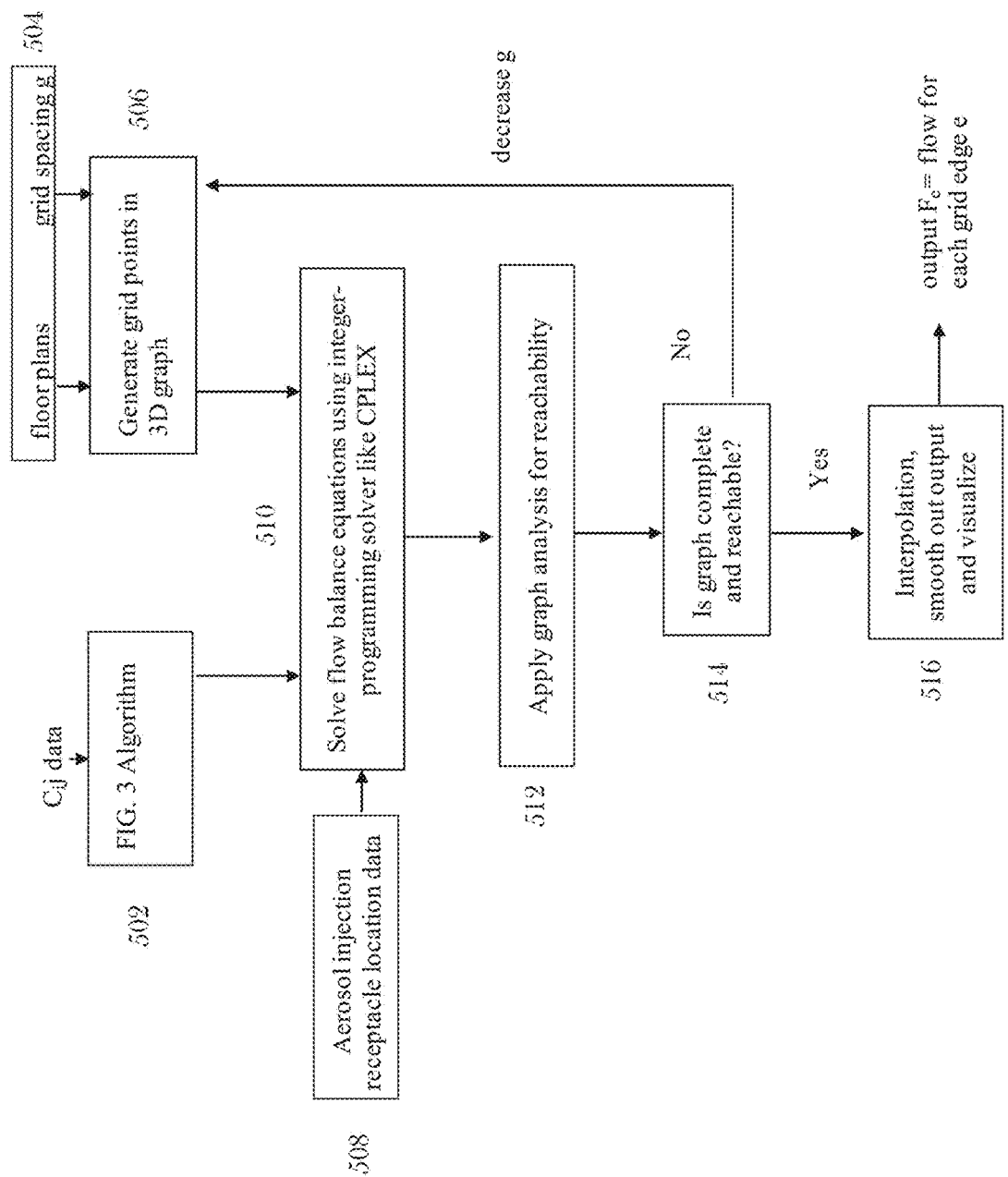
FIG. 5 is a flow diagram illustrating how the present technology performs flow intensity map generation.

FIG. 5 is a flow diagram illustrating how the present technology performs flow intensity map generation. The method of FIG. 5 provides a complete analysis of the air flows in the entire indoor space. This allows careful examination of the spread of aerosols within rooms, across rooms and in common areas and passageways. At step 502, the method described in FIG. 3 is applied. At step 504, the software takes as input a geometric vector representation of the floor plan, and a grid spacing parameter 'g' that can be modified at any time via the server's user interface. The grid spacing parameter 'g' determines the grid resolution: high values imply greater granularity and accuracy but more computation. Then, at step 506, a set of 3D grid points in space, equally spaced according to the grid resolution parameter 'g' is generated. Grid points are also identified with locations of sensor assemblies, injectors and filters.

At step 508, aerosol injection, sensor assembly, and filter location data are obtained via the wireless network from these elements prior to the execution of the step. At step 510, air-flow balance equations are set up for the set of grid points. Each grid point is classified as a source (injector), sink (sensor assembly), filter (location of filter), and waypoint. Between each two grid points is an imaginary edge. The set of such edges and the grid points constitutes a graph or network on which we solve a network flow problem. For this purpose, the flow equations are set up as a constrained integer programming problem and a standard commercial package such as CPLEX is used to solve. The output of CPLEX is used to label each grid edge with a flow. The set of flows thus constitutes the flow balance solution used below.

At step 512, standard packages that solve integer programming problems can report a non-solution or a solution that makes no physical sense. For this purpose, graph reachability analysis is applied to ensure that every edge is carrying some flow. Various criteria can be applied to check whether the solution produced is practical and feasible. For example, if some pathways in the solution carry no flow, that would violate physical realism. The reachability analysis explores graph edges to ensure criteria such as flow balance (even distribution of flow) and non-zero flows. At step 514, if the resulting graph fails the reachability analysis, the grid resolution is too coarse. Accordingly, the parameter 'g' is decreased and the procedure repeated (steps 506 to 512). At step 516, once the flow data satisfies reachability and feasibility conditions, the flow values on the grid edges are used to interpolate heatmap colors and are overlaid on the floor plan. The value 'Fe' will be the resulting flow depicted. When seen by the human eye, the coloring will appear smoothed out (perhaps slightly pixelated) to provide a complete flow map.

Figure 6:
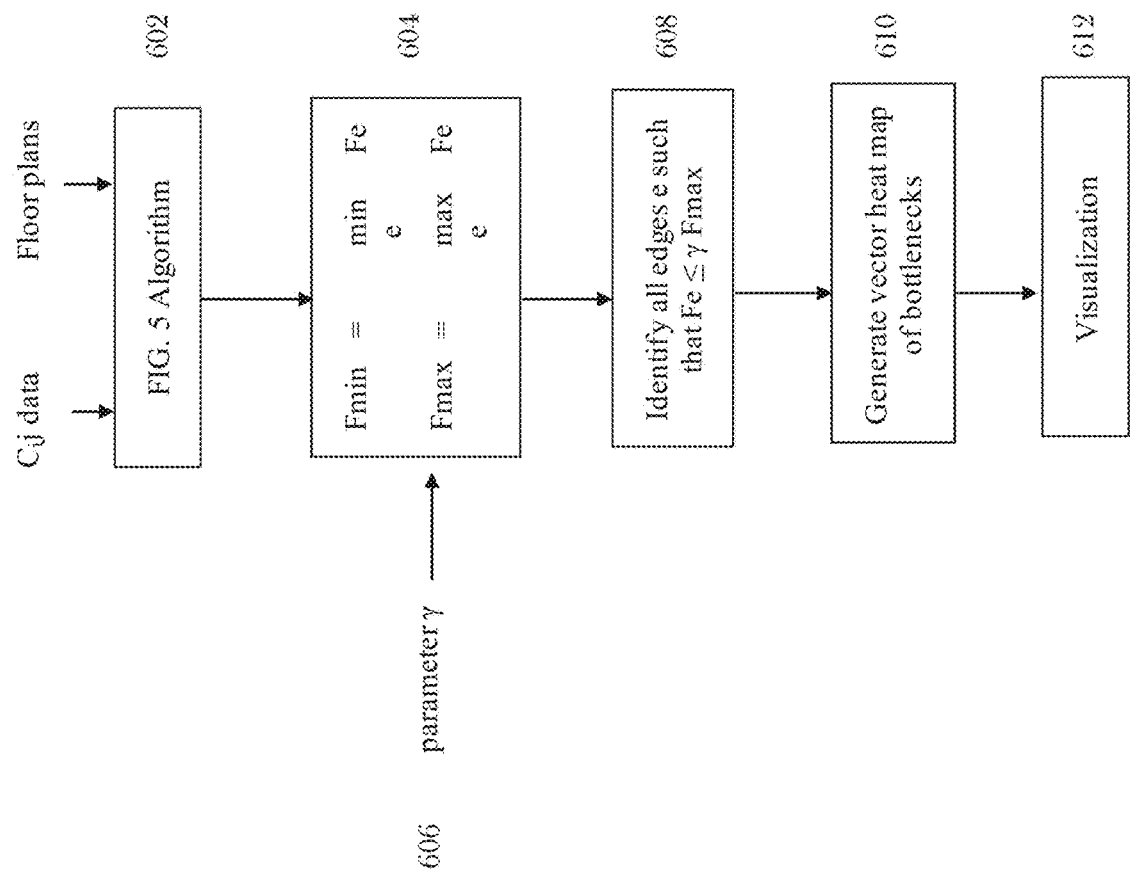
FIG. 6 is a flow diagram illustrating how the present technology performs flow bottleneck identification.

FIG. 6 is a flow diagram illustrating how the present technology performs flow bottleneck identification. The method of FIG. 6 presents the operator with a high-resolution picture of the air-flow bottlenecks. Then, an operator can boost the flow in low-flow areas with additional HVAC or with fans. Similarly, for high-flow bottlenecks, the operator can install our filters in those locations. At step 602, the algorithm described in FIG. 5 is first applied. The resulting 'Fe' values are used below. Thus, as part of this step, control messages are sent from server to injectors and sensor assemblies. Then, Cij values are transmitted back to the server.

At step 604, the min and max flows over the set of edges is computed. At step 606, an input parameter 'y' is obtained from the server's user interface. This parameter, which can be adjusted by the operator through the user interface (via the server), represents the standard to apply for a bottleneck. The higher the value, the looser the criterion for labeling a flow as a bottleneck. Thus, small values identify the most critical bottlenecks. At step 608, the software determines the flow threshold for bottleneck identification. All edges that are below the threshold (thus, low flow) are identified. If the direction of inequality is reversed, we get high-flow edges. If the goal is to maximize the flow of clean air, the bottleneck edges are taken as the low-flow edges. On the other hand, if the goal is to examine the risk of infection or pollutant spread, the bottleneck edges are the high-flow edges. At step 610, a map of bottleneck edges is generated and overlaid on the floor plan. At step 612, connected and adjacent bottlenecks are identified and colored accordingly for visualization.

Figure 7:
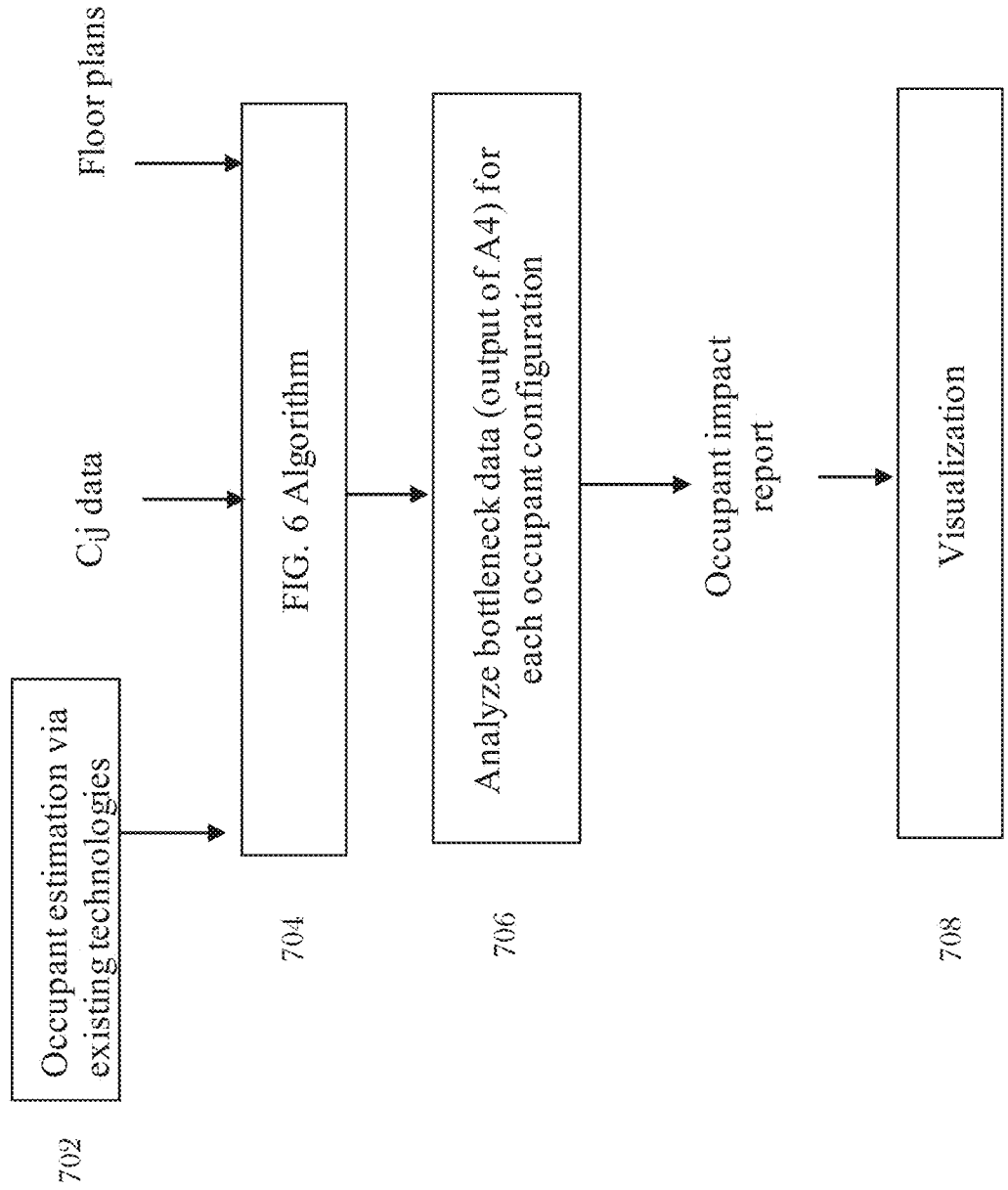
FIG. 7 is a flow diagram illustrating how the present technology performs an analysis of flow bottleneck with occupant impact.

FIG. 7 is a flow diagram illustrating how the present technology performs an analysis of flow bottleneck with occupant impact. The method of FIG. 7 generates two types of occupant risk reports. The first is for low-flow, which identifies areas for mitigating with additional HVAC to increase the quality of air for occupants. For example, high-density areas should receive higher flows of fresh or filtered air. The second type is for risk analysis. If some areas carry flow too easily, then a sick person can infect others easily or a harmful substance may spread too easily. This suggests the installation of filters or barriers.

At step 702, for the purpose of this algorithm, the system makes use of existing infrared technologies for estimating people headcounts in indoor spaces. Then, for a particular configuration of people, the server communicates with the injectors and sensor assemblies to execute the algorithm described in FIG. 6. At step 704, the bottleneck data (low-flow or high-flow) is identified for various such occupant configurations. This identification occurs through the algorithm of FIG. 6. This step computes the union and intersection of bottlenecks across such configurations. At step 706, the bottleneck data from step 704 is used to generate an occupant-risk report that identifies for each occupant the likely quality of air based on the bottleneck analysis and thus, a risk level for low quality air. At step 708, the bottleneck risk values are overlaid on the floor plan and depicted.

Figure 8:
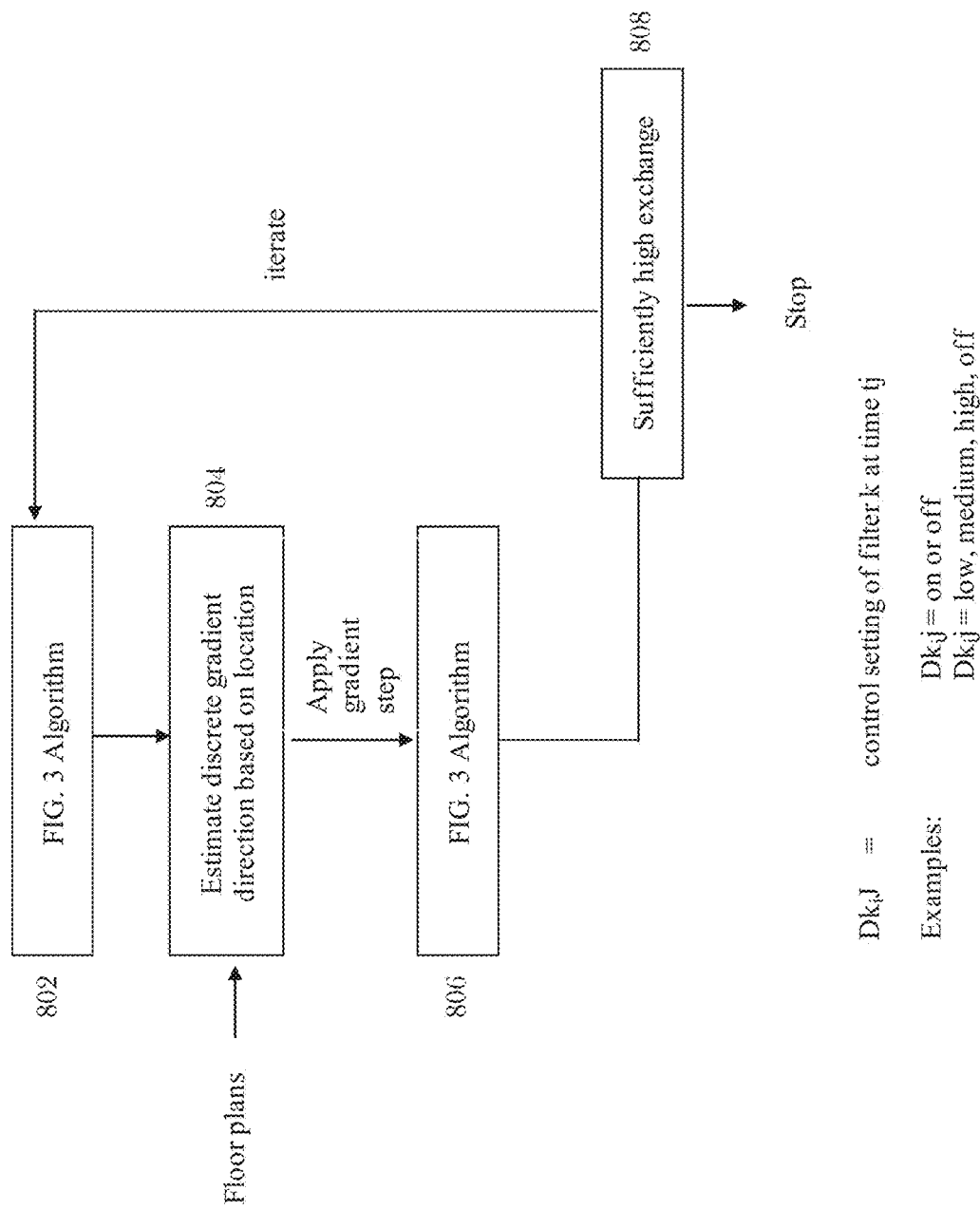
FIG. 8 is a flow diagram illustrating how the present technology provides automated control of distributed portable air filters.

FIG. 8 is a flow diagram illustrating how the present technology provides automated control of distributed portable air filters. The purpose of the method of FIG. 8 is to automatically determine the filter settings and to have the server communicate with each filter to both optimize these settings and operate them at the optimal settings. Air exchange optimization commences at step 802, the software defines the variables $D_{k,j}$ as the control settings for filter k at time tj. These are control values sent from the server over the wireless network to each filter. The values depend on the type of air filter used. Some filters are simple on-off, and others have finer-grained control such as low/medium/high. First, the algorithm of FIG. 3 is run.

Then, at step 804, the floor plan data and the output of the algorithm of FIG. 3 is used in this step to estimate the gradient of change based on filter control. The idea is to use two successive filter settings (for each filter) to assess the partial derivative with respect to the $D_{k,j}$ for that filter. At step 806, the gradients are used to determine the next set of control values issued by the server to the filters via the wireless network. Each computed gradient is used as a proxy for the direction of change (increase or decrease) for the given variable the gradient is being evaluated. Thus, filter's operating fan speed can be increased if the gradient for its speed shows improvement for the desired goal of the moment, whether it is to reduce bottlenecks or increase exchange rates. At step 808, the algorithm of FIG. 3 is applied again. If the new exchange rates are sufficiently high, as determined by preset criteria, for example with the parameter α in FIG. 3, the algorithm terminates and outputs the current settings. Otherwise, it iterates further until such settings are discovered.

Figure 9:
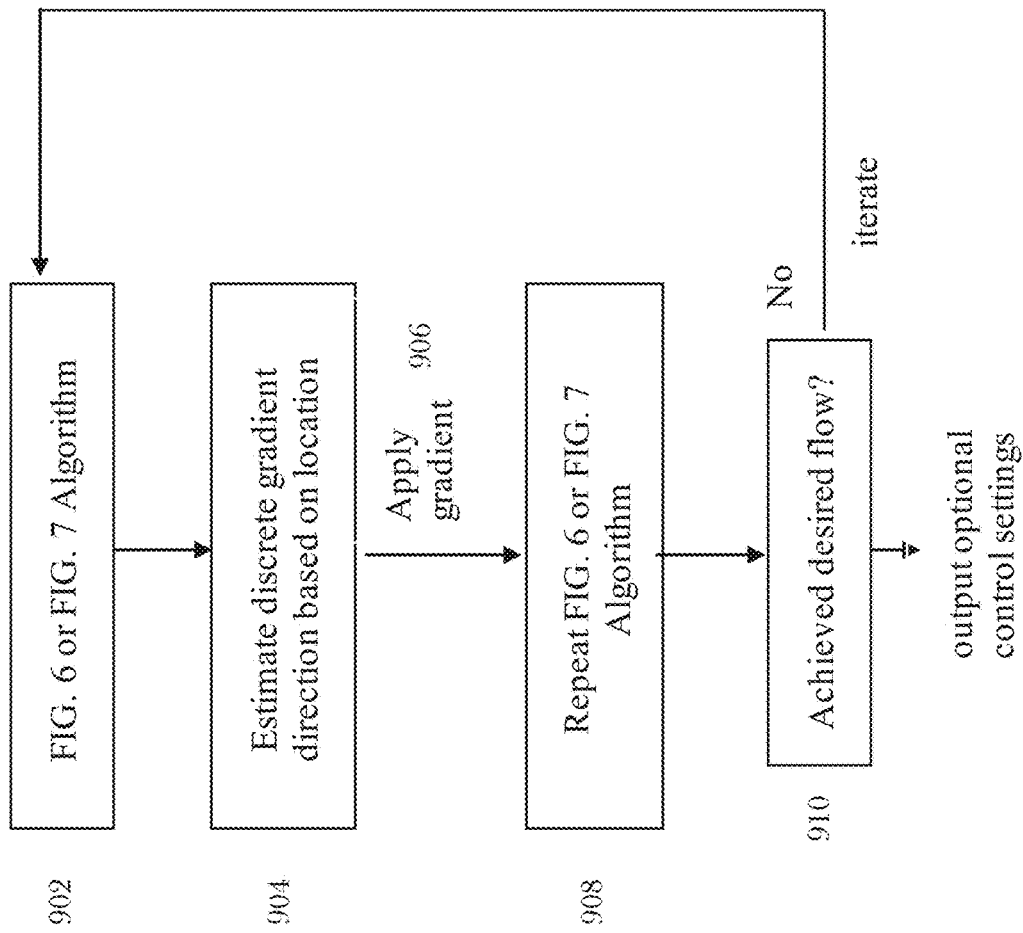
FIG. 9 is a flow diagram illustrating how the present technology provides techniques for arriving at optimal filter settings to reduce bottlenecks.

FIG. 9 is a flow diagram illustrating how the present technology provides techniques for arriving at optimal filter settings to reduce bottlenecks. The optimal filter settings are then sent by the server to each filter over the wireless network. At step 902, the software executes the algorithm of FIG. 6 or FIG. 7, depending on the desired output. At step 904, the software estimates discrete gradient based on $D_{k,j}$ settings as explained in FIG. 8. At step 906, the software applies the gradients to increase or decrease the $D_{k,j}$ settings based on the sign and magnitude of the gradients. For example, during minimization (bottleneck reduction), a negative gradient for a particular $D_{k,j}$ setting suggests incrementing the value whereas a positive gradient recommends a decrementing the value. At step 908, depending on which one was selected, the algorithm of FIG. 6 or FIG. 7 is repeated. At step 910, if the desired optimality is achieved (with very little effect on the gradients) then the software stops and outputs the current iteration's $D_{k,j}$ settings. Otherwise, the software continues iteration until the desired optimality is achieved.

Figure 10:
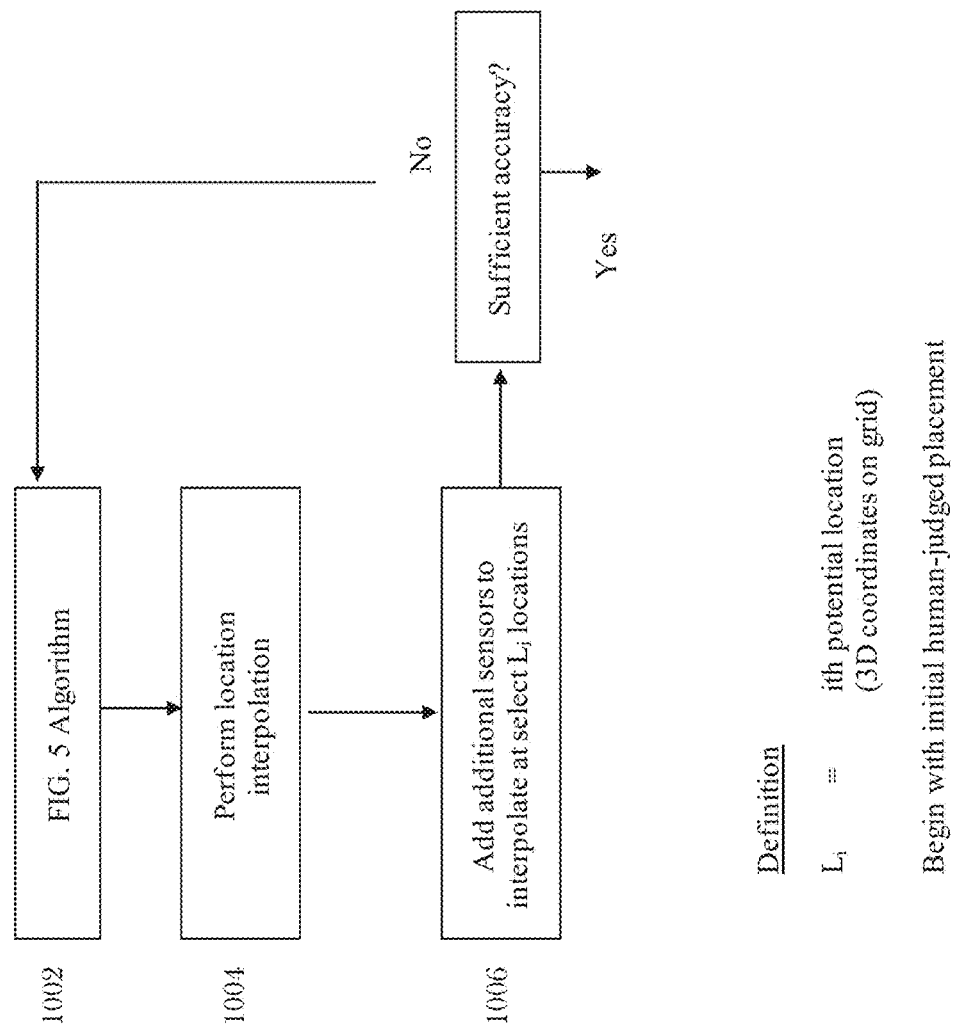
FIG. 10 is a flow diagram illustrating how the present technology provides techniques for optimizing the locations of additional sensor assemblies for better accuracy and resolution.

FIG. 10 is a flow diagram illustrating how the present technology provides techniques for optimizing the locations of additional sensor assemblies for better accuracy and resolution. At step 1002, Li is defined as the ith potential location. Each such location is a grid point based on the grid generated in the algorithm of FIG. 5, which is executed first to determine these locations. At step 1004, the output of the algorithm of FIG. 5 is then used to perform location-interpolation. First, an accuracy estimate is derived from the output of the algorithm of FIG. 5. Then, at step 1006, additional sensor locations are determined based on spatial location data and the Li values. If the number of sensors are budget-limited, the locations are rank-ordered by their contribution to accuracy.

At step 1008, if the accuracy determined is sufficiently high, the algorithm halts and the Li values are output. Otherwise, further iterations are performed until either the budget runs out or the desired accuracy is achieved. Various criteria for accuracy can be applied, at the choice of the operator. For example, a commonly used criterion is to stop when the change in accuracy is minimally effective. In practice, such systems are likely to be calibrated in real-world settings and those will result in data about typical accuracies that can be used by customers.

Figure 11:
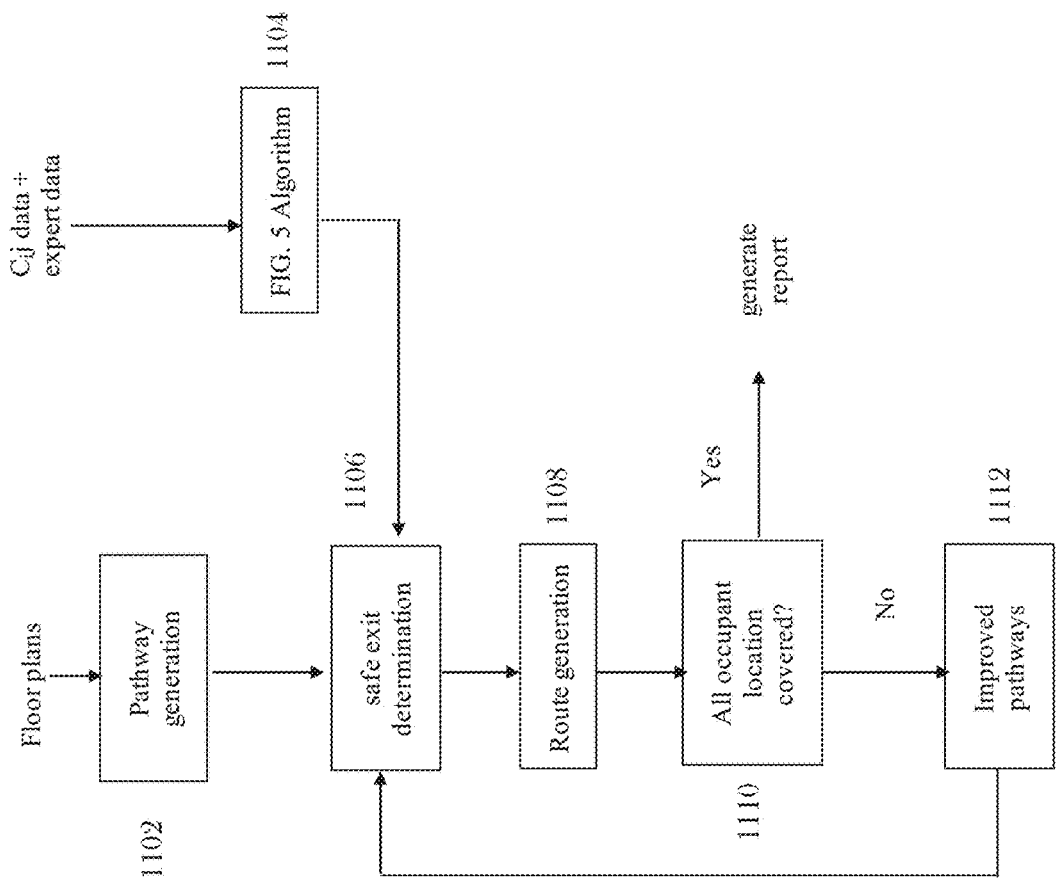
FIG. 11 is a flow diagram illustrating how the present technology provides evacuation planning for high-intensity air events with trouble spots and ACH estimations illustrated.

FIG. 11 is a flow diagram illustrating how the present technology provides evacuation planning for high-intensity air events. The method of FIG. 11 discloses techniques to compute exit pathways for evacuations when, for example, a dangerous element is released in an indoor setting. The pathway computation can be done ahead of time, and in real-time as the sensors detect hazards. The software commences at step 1102, where the geometric floor plan data is processed to generate paths for people from every potential entry/exit point of the building or area to every potential destination (rooms). This part slightly modifies well-known path finding algorithms already published in textbooks (such as Dijkstra's algorithm). At step 1104, the algorithm of FIG. 5 is executed.

At step 1106, once the flow data from the algorithm of FIG. 5 is known, the edges in the pathway data are labeled with flow values so that the total flow is known along all potential pathways. There are many ways this can be calculated. One simple way is to apply a weighted pathway algorithm using the flows as weights. Then, for a given level of safety (flow-level), the paths are pruned until safe pathways are found from every destination (room) to an exit point. At step 1108, the routes determined based on exit pathways in step 1106 are listed and generated.

At step 1110, the software examines coverage: are all rooms covered in the exit pathway determination? If so, the software stops and reports the pathways. In a live-alarm situation, the server can broadcast this via a public announcement system or can wirelessly turn on lights accordingly. At step 1112, if not every room is covered, then the uncovered rooms are processed by the software to determine pathways from them to the main exit points. This can be done by modifying a standard route-finding algorithm so that each uncovered room is treated as the sole point from which to determine efficient exit routes. Then the resulting routes are coalesced and sorted to reduce unnecessary overlap.

FIG. 12 is a diagram illustrating an example application of the present technology to a space with low built-in airflow with a supplemental portable filter. This example shows the capabilities of this technology and illustrates a number of the technical concepts introduced earlier in the application, including local ACH, types and identification of hotspots, spatial and temporal heterogeneity. The image in the center is the intensity vs. time plot for each of the sensors. Each subplot has the data from a single sensor assembly plotted, one over another, and arranged from top to bottom in the same order as the sensor assemblies are overlaid on the floorplans as horizontal rows of dots 1202. The dark lines link the data on the time plot to the position in the room at which it was measured. For example, the line connects the temporal-spatial data measured at starting time on second row of plots 1204 to the spatial contours at the second row of sensors 1202.

In this scenario, the filter reduces to low value the concentration of particles in the center of the room and clears particles with a flow to the center. In FIG. 12, five sensor assemblies were distributed uniformly in a residential bedroom to make maps of the aerosol flow in the room. The injector, placed at the front of the room (top of each floorplan view), was turned off and on manually, and the actuator was a portable filtration device set to high, medium, and low speeds. The ventilation was minimal with climate control provided by radiant heat. This is a typical low flow-rate environment with an exchange of about 0.3 air changes per hour (ACH). The room was set up with a Corsi box, a portable MERV-13 filter (B.F) located in the center of the room. An aerosolized solution of 5% glycerin was injected from the desk at the front of the room and turned on at times 7 min, 47 min, and 87 min and turned off at times in between, at 27 min, 67 min and 107 min.

Aerosol concentrations were measured by each of 5 sensor assemblies (horizontal gray bars), each connected to 5 PM2.5 sensors located at each of the solid dots. Data were measured at 5 Hz, and averaged for 30 s intervals to produce a sequence of contour maps. The maps from 3, 8, 17, 25, 33, and 41 minutes are shown here. Also produced were false-color maps stacked into a time-lapsed movie (not show here). The graphs at the center of FIG. 12 are the raw data measured by each of the 5 sensors in each of the 5 sensor assemblies, arranged from top to bottom in the same order as appears in FIG. 12.

Initially, at t=3.3 minutes, the aerosol concentration 1204 is uniformly close to zero across the entire room, hence there are no contour lines 1202. The aerosol concentration begins to rise by 8.3 minutes 1206, with a gradient that is high at the front of the room and flattening to lower values towards the back. In the center of the room, a trouble spot, a bottleneck, 1206 is forming due to the high flow rate of air being pulled from all points in the room into the filter 1203, here shown at about the center of the room. This would be a problematic place for a healthy person if an infected person is anywhere in the space since air from all over the room flows past the filter. Accordingly, the bottleneck can be remediated, for example, by strategic placement of people, seating or by modifying ventilation control.

Eventually, the aerosol concentration reaches a peak value when the number of particles entering any particular space on the contour map is the same as the number leaving. Though the time plot shows a constant plateau 1212, the contour map is evidence that there are still gradients, with a trouble spot forming, a hot spot due to still air at the back of the room 1214. At this point, the injector is turned off and the room begins to clear. It is notable that peaks values at 17, 57, and 97 minutes rise as the filter-fan speed is reduced from high to medium to low speed.

As the room begins to clear, the time plots show a steady decrease 1210 and the left-right gradient is less pronounced than it was as the concentration of particles was increasing 1206. Comparing the slope at the center of the room 1209 to that at the front 1207 shows that the local ACH at the center 1209 of the room is higher than at the front 1207. The trouble spot at the back of the room is still visible at 24.9 minutes 1208, remains at 33.4 minutes 1210, and finally does go away when the room is cleared at 41.4 minutes 1216.

The data show that at lower speeds, a higher concentration of aerosols is reached, and that the Corsi box is effective at filtering aerosols from the room. With the fan off, the aerosol level would remain high for more than 2 hours. The maps show the flow of the aerosols from the front to the back of the room and represent the inhomogeneity of both the room filling and clearing. FIG. 12 thus demonstrates that a distributed network of sensors provides a rich variety of real-time information across a spatial indoor area.

FIGS. 13 and 14 are diagrams illustrating an application of the present technology to a classroom showing aerosol measurements. FIGS. 13 and 14 show measurements and inferences made from a typical classroom setting. The thin curved lines represent contours of aerosol concentrations. The contours help understand evaluate whether additional sensor assemblies can increase accuracy. As shown in FIG. 13, 2 sensor assemblies with 5 sensors each were distributed in a classroom to make maps of the aerosol flow, on a grid of desks spaced 5 feet apart, while the sensors are placed alternate desks and 10 or more feet apart (represented by black dots). The injector was turned off and on manually, and the actuator was the BlueAir model 211, was set to high, medium, and low speeds. The ventilation was moderate with climate control provided by recirculating HVAC. This is a typical educational flow-rate environment with an exchange of about 3 ACH. An aerosolized solution of 5% glycerin was injected from the front of the room and turned on and off for roughly 40 minute periods of 20 min on and 20 min off.

Aerosol concentrations were measured by each of 10 locations indicated by solid dots. Since the sensor assemblies were set up in random order to test the mapping and interpolation software, it was not possible to clearly connect each spot to a sensor assembly's data output. Data were measured at 5 Hz, and averaged for 30 s intervals to produce a sequence of contour maps. The maps from 13, 17, 30, 33, 41, and 50 minutes are shown here as 1402, 1404, 1406, 1408, 1410, and 1412, respectively. The graphs shown in two places are to give a general sense of the data and the times at which maps are produced are indicated by vertical dumbbells on each of the times 1414 listed above. The data show that at lower filtration speeds, significantly higher concentration of aerosols is reached, and that the unit is effective at filtering aerosols from the room. With the unit off, the aerosols would still be cleared, but requiring approximately twice the time. The maps show the flow of the aerosols from the front to the back of the room with some homogeneity due to a rightward flow of the air from the HVAC system, leading to a lingering of the aerosols in the front-left corner of the room, revealing a hot spot with lower, local ACH, due to the stiller air in that part of the room 1416.

FIG. 13 can be compared to FIG. 14, but in the former, data for the sensors in the second and fourth rows was removed before making the interpolated contour maps. Thus, the identical conditions are illustrated in FIGS. 13 and 14, except with a higher density of sensors in the latter. The distance between desks (squares) is five feet, but now the sensors (black dots) are on a 10-foot grid. The resulting contours show a significantly more pronounced left-right asymmetry in FIG. 14—1316 vs., 1416. The top-bottom asymmetry is still evident, though the gradient is markedly steeper in FIG. 14—1316 vs., 1416, to show that adding sensors reveals more detail of the spatial heterogeneity of aerosol spread. A situation with an intentionally high gradient of aerosol concentration was created by placing an effective portable filtration device, the BlueAir model 211, in the center. The data show a strong left-right asymmetry, which is not nearly as pronounced in FIG. 13 when the grid-spacing is increased by removing 4 of the sensors.

Indeed, FIGS. 13 and 14 clearly show that a higher density of sensors, in the right locations, results in significantly different contours. What this illustrates is that the traditional single-sensor-in-a-room or attendant-walking-with-a-sensor is likely to produce inaccurate assessments of air quality. Interestingly, infection risk calculations use a Wells-Riley model assume that the pathogen is uniformly mixed in the room (https://doi.org/10.1073/pnas.2018995118), based on the global ACH value for the entire space. Our application shows that the local ACH can and should be used to calculate risk of infection at various hot spots in a room. This unique capability will be useful many setting such as health care, where the unhealthy/high-risk hot spots in a patient's room can be identified, relative risk calculated, and appropriate remediation made.

The foregoing description and drawings should be considered as illustrative only of the principles of the disclosure. The disclosure is not intended to be limited by the preferred embodiment and may be implemented in a variety of ways that will be clear to one of ordinary skill in the art. Numerous applications of the disclosure will readily occur to those skilled in the art. Therefore, it is not desired to limit the disclosure to the specific examples disclosed or the exact construction and operation shown and described. Rather, all suitable modifications and equivalents may be resorted to, falling within the scope of the disclosure. All references cited herein are incorporated by reference in their entirety.

The invention claimed is:

1. A system for optimizing air flow within a closed environment, said system comprising:
    a plurality of injectors in the closed environment and configured to expel aerosol particles into the closed environment;
    a plurality of discrete sensor assemblies in the closed environment, each having a sensor processor and one or more sensors configured to independently and dynamically detect the expelled aerosol particles in the closed environment and provide detected aerosol particle data, wherein the sensor processor of each of said plurality of discrete sensor assemblies is configured to dynamically, and in real time, convert detected aerosol particle data from the one or more sensors to sensed concentration data; and
    a system processor configured to dynamically receive the sensed concentration data from the sensor processor for all of the plurality of discrete sensor assemblies, dynamically operate said plurality of injectors in real-time to expel aerosol particles into an environment in response to the sensed concentration data, dynamically generate a flow intensity map that maps uniformity and rate of air changes per hour in the closed environment and maps regions of low air exchange based on positions for the one or more sensors in the closed environment;
    said system processor further configured to, based on the flow intensity map, dynamically determine areas of high risk of infection in the closed environment, verify the need for a remediation step, and if a remediation step is needed to dynamically determine a remediation recommendation for the closed environment to correct for non-uniformity, rates of air changes per hour, and regions of low air exchange, and said system processor further configured to verify efficacy of the recommended remediation.

2. The system of claim 1, wherein said system processor dynamically operates said plurality of injectors to turn ON, turn OFF, adjust concentration, or adjust velocity to simulate events and dynamically determine an impact of those events.

3. The system of claim 1, wherein said sensor processor of each of said plurality of discrete sensor assemblies operates said plurality of injectors independent of the system processor.

4. The system of claim 1, wherein air flow is changed to optimize aerosol particle concentration using one or more actuators.

5. The system of claim 4, wherein feedback from the one or more actuators is collected by the system processor.

6. The system of claim 5, wherein the feedback from the one or more actuators is used by the system processor to modulate a quantity of the aerosol particles expelled by said plurality of injectors.

7. The system of claim 4, wherein the system processor is networked to the one or more sensors, the said plurality of injectors, and the one or more actuators.

8. The system of claim 1, wherein said plurality of discrete sensor assemblies are configured to locally monitor aerosol generation, clearance, and movement.

9. The system of claim 1, further comprising one or more auxiliary sensors that detect any one of volatile organic compounds, ozone, and $CO_2$.

10. The system of claim 1, further comprising one or more air filters, wherein the system processor activates the one or more air filters to maintain the aerosol particle concentration within a predetermined range.

11. The system of claim 1, wherein the recommendations include use of air filters, sensors, or HVAC (heating, ventilation and air conditioning).

12. The system of claim 1, wherein the regions of low air exchange are based on a low rate threshold.

13. A method for air flow optimization in a closed environment, the method comprising:
- directing one or more injectors in the closed environment to expel aerosol particles into an environment;
- independently and dynamically detecting the aerosol particles using one or more discrete sensor assemblies in the closed environment, wherein a sensor processor of each of the plurality of discrete sensor assemblies dynamically and in real time converts electronic data to sensed concentration data;
- dynamically receiving the concentration data from the sensor processor of each of the one or more sensor assemblies at a system processor, wherein the system processor directs the one or more injectors in real-time to expel aerosol particles into an environment in response to the sensed concentration data;
- generating a flow intensity map to map uniformity and rate of air changes per hour in the closed environment and maps regions of low air exchange based on positions for the one or more sensor assemblies;
- dynamically determine, based on the flow intensity map, areas of high risk of infection in the closed environment and a remediation recommendation for the closed environment to correct for non-uniformity, rates of air changes per hour, and regions of low air exchange; and
- altering air flow in the environment in response to the remediation recommendation, to optimize aerosol particle concentration using one or more actuators.

14. The method of claim 13, wherein the one or more sensor assemblies have one or more sensors.

15. The method of claim 14, further comprising one or more auxiliary sensors that detect any one of volatile organic compounds, ozone, and $CO_2$.

16. The method of claim 14, wherein the system processor is networked to the one or more sensors, the one or more injectors, and the one or more actuators.

17. The method of claim 14, further comprising identifying regions of low air exchange by determining geographical locations for the one or more sensors and interpolating a heatmap visualization of the low air exchange regions.

18. The method of claim 13, wherein the sensor processor of each of the one or more sensor assemblies operates the one or more injectors independently of the system processor.

19. The method of claim 13, further comprising collecting feedback from the one or more actuators at the system processor, wherein the feedback from the one or more actuators is used by the system processor to modulate a quantity of the aerosol particles expelled by the one or more injectors.

20. The method of claim 13, wherein the one or more sensor assemblies are configured to locally monitor aerosol generation, clearance, and movement.

21. The method of claim 13, further comprising activating one or more air filters in a manner that maintains aerosol particle concentration within a predetermined range.

* * * * *